(12) United States Patent  
Wachter

(10) Patent No.: US 8,141,551 B2
(45) Date of Patent: Mar. 27, 2012

(54) MOUTHPIECE AND FLOW RATE CONTROLLER FOR INTRAPULMONARY DELIVERY DEVICES

(75) Inventor: Allan M. Wachter, Tempe, AZ (US)

(73) Assignee: Destal Industries, Inc., Columbus, IN (US)

( * ) Notice: Subject to any disclaimer, the term of this patent is extended or adjusted under 35 U.S.C. 154(b) by 1077 days.

(21) Appl. No.: 12/032,181

(22) Filed: Feb. 15, 2008

(65) Prior Publication Data

US 2008/0196716 A1  Aug. 21, 2008

Related U.S. Application Data

(60) Provisional application No. 60/890,439, filed on Feb. 16, 2007.

(51) Int. Cl.
*A61M 11/00* (2006.01)
*B05B 1/26* (2006.01)

(52) U.S. Cl. ......... 128/200.18; 128/200.14; 128/200.23

(58) Field of Classification Search ............. 128/200.14, 128/200.18, 200.22, 200.23, 203.15, 203.23, 128/203.24
See application file for complete search history.

(56) References Cited

U.S. PATENT DOCUMENTS

| | | | |
|---|---|---|---|
| 4,470,412 A * | 9/1984 | Nowacki et al. ......... 128/200.18 |
| 4,534,343 A | 8/1985 | Nowacki et al. | |
| 4,809,692 A | 3/1989 | Nowacki et al. | |
| 4,915,242 A * | 4/1990 | Marte ......................... 215/11.1 |
| 5,375,593 A | 12/1994 | Press | |
| 5,810,003 A | 9/1998 | Findlater | |
| 5,824,012 A * | 10/1998 | Burchett et al. .............. 606/236 |
| 5,843,030 A * | 12/1998 | Van Der Merwe ............. 604/77 |
| 5,899,201 A * | 5/1999 | Schultz et al. ........... 128/200.23 |
| 5,904,140 A | 5/1999 | McGoogan | |
| 6,065,472 A * | 5/2000 | Anderson et al. ........ 128/203.21 |
| 6,085,742 A | 7/2000 | Wachter et al. | |
| 6,347,629 B1 * | 2/2002 | Braithwaite ............. 128/203.15 |
| 6,557,548 B1 | 5/2003 | Dickson | |
| 6,626,168 B1 | 9/2003 | Carroll et al. | |
| 6,681,768 B2 * | 1/2004 | Haaije de Boer et al. ........................ 128/203.15 |
| 6,776,157 B2 | 8/2004 | Williams et al. | |
| 6,857,427 B2 | 2/2005 | Ziegler et al. | |
| 6,904,906 B2 | 6/2005 | Salter et al. | |
| 7,134,432 B2 | 11/2006 | Olsen | |
| 7,360,537 B2 * | 4/2008 | Snyder et al. ............ 128/200.23 |
| 2006/0090751 A1 | 5/2006 | Walker | |

* cited by examiner

*Primary Examiner* — Kristen Matter

(74) *Attorney, Agent, or Firm* — Stinson Morrison Hecker LLP

(57) ABSTRACT

This invention relates to a therapeutic device and method of administering precisely measured doses of a therapeutic substance via inhalation to pediatric and adult patients. More specifically, the invention relates to a therapeutic device and method of administering inhaled medication which delivers a controlled flow rate to a mouthpiece for administration of medicament to young children and adults with a diminished capacity, at a rate of about 25.8 L/minute to 30.2 L/minute.

19 Claims, 4 Drawing Sheets

MOUTHPIECE AND FLOW RATE CONTROLLER FOR INTRAPULMONARY DELIVERY DEVICES

CROSS-REFERENCE TO RELATED APPLICATIONS

This application is based on and claims priority to U.S. Provisional Application Ser. No. 60/890,439, filed on Feb. 16, 2007, which is hereby incorporated herein by reference.

STATEMENT REGARDING FEDERALLY SPONSORED RESEARCH OR DEVELOPMENT

Not applicable.

BACKGROUND OF THE INVENTION

1. Field of the Invention

This invention relates to a therapeutic device and method of administering precisely measured doses of a therapeutic substance via inhalation to pediatric and adult patients. More specifically, the invention relates to a therapeutic device and method of administering inhaled medication which delivers a controlled flow rate to a mouthpiece for administration of medicament to young children, the elderly and other adults with a diminished capacity.

2. Description of Related Art

There is a need for an accurate mechanism for delivering precise drug dosages of inhalable medicaments into the lungs of persons with reduced lung capacity. It is standard medical procedure to treat humans afflicted with pulmonary conditions by administering medicament inhalable into the lungs. For example, asthma is a condition characterized by symptoms wherein the airways of the lungs become narrowed, inflamed and filled with mucous such that the patient experiences wheezing, coughing, and shortness of breath.

Examples of inhalable medicaments used in the treatment of asthma include bronchodilators and anti-inflammatories such as corticosteroids. Other types of inhalable medicaments for different medical conditions include insulin, proteins and polypeptides, enzymes, anticholinergics, antibiotics, antifungals, antivirals, beta-2 agonists, mucolytics and others.

One of skill in the art understands that it is important to control the flow rate of an inhaled medicament so that a defined, consistent, metered (i.e., quantifiable) dose may be administered to the patient. Presently, one of the most popular delivery devices is the pressurized propellant driven metered dose inhaler ("pMDI") which is typically comprised of a canister containing a mixture of propellants, surfactants, preservatives and one or more active pharmaceutical compounds. The pMDI releases a metered dose of aerosolized medicine upon each actuation. (The contents of the canister of the pMDI and/or the pharmaceutical compounds with or without carriers or excipients are examples of what are sometimes referred to herein as "medicament" or "medicaments.")

When used frequently, however, pMDIs have certain drawbacks, such as they tend not to permit the administration of defined dosages of the medicament substance for a variety of reasons. Accessories have been developed in an attempt to overcome these drawbacks. Devices called spacers are often used as accessories with pMDIs for the purpose of providing a contained space or holding chamber between the mouth of the patient and the pMDI nozzle from which the medicament is dispensed. Spacers typically are hollow cylinders with open ends. The spacer or holding chamber is used by placing it in the mouth and the patient pursing his or her lips around it, so that a relatively airtight seal is formed between the mouth and the mouthpiece/nozzle of the holding chamber device or spacer. Once such a seal is formed, the pMDI is actuated, releasing aerosolized medicament into the spacer or holding chamber device from which the patient inhales the medicament. Spacers help to capture the gas emitted from a pMDI but do not facilitate inspiration after actuation of the pMDI. It should be noted that pMDIs may be used without a spacer or holding chamber by actuating the pMDI about 2 inches in front of the mouth of the patient, who inhales the aerosol emitted by the pMDI.

An improvement on the spacer device discussed above is a valved holding chamber device, which is similar to a spacer but contains a one-way, low-resistance valve that allows the vaporized or atomized medicament to remain within the body of the chamber until the patient inhales, resulting in the valve opening and permitting the medicament to enter the lungs.

Both spacers and holding chambers have the disadvantage that it is very difficult to ensure that the patient has inhaled the correct dosage of the medicament. Reasons for this include, but are not limited to, the tendency of the medicament to settle via gravity out of the aerosol "mist" to the bottom of the spacer or holding chamber. This settling negatively affects the overall amount of medicament available to inhale, as well as the proportion of "respirable particle size" available to inhale. Respirable particle size refers to the ideal size of inhalable particles; the ideal size is in the range of approximately 1.5 to 2.5 microns. Another disadvantage of the spacers and holding chambers is the patient tends to have difficulties properly timing the release of medicament into the spacer or holding chamber so that the patient inhales at the proper moment.

The aforementioned deficiencies in administering desired dosages of an inhalable medicament led to the inventor's improved holding chamber device disclosed in U.S. Pat. No. 6,085,742 ("the '742 Patent), the disclosure of which is incorporated herein in its entirety by reference. The '742 Patent discloses an intrapulmonary device providing a means for controlling the flow rate so that the inhaled medicament is administered and taken into the patient's lungs in a manner which greatly reduces or even eliminates overdosing and underdosing.

When inhalation devices, including the holding chamber disclosed in the '742 Patent, are used by children, or adults with reduced lung capacity, the accuracy of reported doses and/or amount of drug used in the treatment of a pulmonary disease is unreliable. An overdose or an underdose can have undesirable effects on the patient. A patient can have adverse reactions if too large a dosage of the medicament is inhaled. Conversely, if the patient does not inhale the entire dosage, the medicament may be partially or entirely ineffective to treat the condition for which it was administered.

The device of the '742 Patent, while easy to use and efficient for the administration of medicaments to adults and older children is less reliable when used with children younger than about six years of age. Given that at present about 60% of asthma patients are between the ages of one and five, there is a significant need for a device which will overcome the aforementioned drawbacks of the prior art. A device which can be readily used on patients as young as two years old, or even younger, as well as adults with significantly diminished lung capacity is highly desirable.

It is also highly desirable to have an improved device for readily administering intrapulmonary medicaments to pediatric patients and adults with a diminished capacity for inhaling who are unable to effectively use a pMDI.

Intrapulmonary medication delivery to young children has been attempted by physicians, nurses, respiratory technicians, and other clinicians using many different devices, such as nebulizers, holding chambers, spacers, pMDIs, and dry powdered inhalers ("DPIs"). Currently, the accepted method of delivery using pMDIs for young children of ages five years or less, or to the elderly or others having reduced ability to create sufficient inspiratory flow to use an MDI or pMDI, is to use a spacer device or holding chamber device along with a facemask. Masks usually come in different sizes to accommodate the different ages and/or sizes of patients' faces.

One of the main difficulties in correctly administering inhaled medication results from the inability of some patients to generate consistently low inspiratory flow rates. Most patients inhale at very high inspiratory flow rates in an effort to inhale their entire medicament; this results in a turbulent flow pattern rather than a more desirable laminar flow pattern which provides the best administration of the medicament. Inhaling at a low inspiratory flow rate (30 L/min or less) is equivalent to normal tidal breathing (tidal breathing is a term which describes inhaling and exhaling through the same opening). Many studies in children and especially in children with compromised lung conditions, e.g., Cystic Fibrosis, asthma or other chronic lung diseases ("CLDs"), indicate that low inspiratory flow rates aid in the desirable deep penetration of medication into the pulmonary cavities of the lungs.

Moreover, the proper timing of actuating and inhaling medication from a pMDI is difficult to master for very young children and the elderly. Although spacers and holding chambers are helpful, they do not necessarily result in correct flow rates. In an effort to encourage patients to inhale at correct flow rates, most spacers and holding chambers are equipped with so-called coaching whistles, which actuate at high flow rates to provide an audible signal to the adult or pediatric patient that the flow rate is too high, reminding them to slow down their inspiration. Unfortunately, many children like to hear the whistle, and so intentionally breathe in at a high rate to cause the whistle to sound, thus defeating the purpose of the coaching whistle. These whistle mechanisms are also often used in conjunction with masks and in pMDIs.

Masks, while quite useful, have additional drawbacks. In order for masks with accessory devices to properly work, the masks must have a tight fit on the patient's face. This is not always accomplished with the different masks that are currently on the market. Articles have been published claiming that only extremely tight masks will have a tight enough fit to get medication into the lungs. Masks that leak cause significant problems. Leaked medication decreases effectiveness of the administration of the medication to the patient, and may cause eye irritation as well as resulting in spillage and wasting of medication. Another disadvantage of using a mask is dead space, which is defined as the amount of air that fills the facemask when the mask is placed on the patient's face. Facemask dead space has been measured as being 20-100 mL in volume. The higher the dead space volume, the less medicament reaches the lungs of the patient.

Still another problem with the use of masks is that children tend to find the masks uncomfortable and/or frightening to wear, and therefore do not like having them placed over their mouths and noses. When a mask is used, children tend to have the sensation that they are being smothered, and often resist placement and/or maintenance of the mask on their face.

Still yet another problem with masks is that crying inhibits the child's ability to inhale. In fact, multiple studies have shown that crying infants and toddlers cannot properly inhale medication, leading to insufficient deposition of medication into the lungs.

In spite of the aforementioned drawbacks, masks have been used with nebulizers for at least thirty years. Nebulizers are simple mechanical devices which disperse liquid and/or dry medications into fine particulates which may be inhaled. Nebulizers can be air driven, ultrasonically powered or use vibrating membranes. Although all nebulizers can deliver a superior fine particle dose (as compared to pMDIs) to the mask or traditional mouthpiece of an inhaler, they cannot assure improved penetration to the lungs if a child refuses treatment, cries, or the mask leaks.

Still another problem with nebulizer use is the length of time it takes to inhale medication. It can take anywhere from 10-20 minutes to adequately inhale medication through a nebulizer. As noted above, the difficulty that children have in keeping masks on for this period of time further complicates the use of a nebulizer and increases the time required.

The current invention solves at least some of the problems associated with the administration of intrapulmonary medicaments to young children and adults with diminished lung capacity. An object of the invention is to provide an easily usable, effective device that promotes medication administration compliance, for administering accurate metered dosages to pediatric and other types of patients.

SUMMARY OF THE INVENTION

According to the present invention, there is provided a new mouthpiece and flow rate controller for use with devices that are used for administering a dispensable medicament powder or liquid composition for inhalation by a patient. The devices of the present invention can be used with spacers and holding chambers in combination with aerosol delivery devices such as pMDIs and DPIs, as well as with nebulizers. The devices can also be modified for use with other types of intrapulmonary delivery devices, such as those for aerosol delivery of insulin. The mouthpiece and flow rate controller provide a means for administering medicament to a user at a flow rate of about 25.8 L/minute to 30.2 L/minute (0.43 L/second to 0.51 L/second).

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DESCRIPTION OF THE DRAWINGS

FIG. 4A is a top view of the container showing the neck portion; FIG. 4B is a vertical cross section taken through the container with the end boot shown in elevation; FIG. 4C is another vertical cross sectional view of the container with the baffle structure shown in elevation;

DESCRIPTION OF THE PREFERRED EMBODIMENTS

Figure 1:
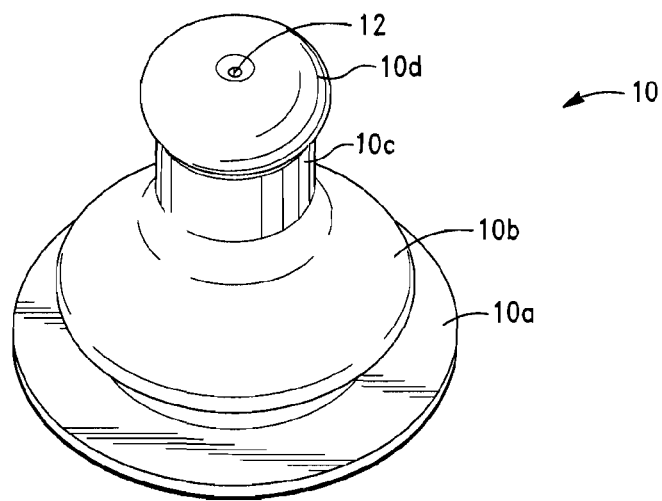
FIG. 1 is a perspective view of the mouthpiece of the present invention.
Figure 2:
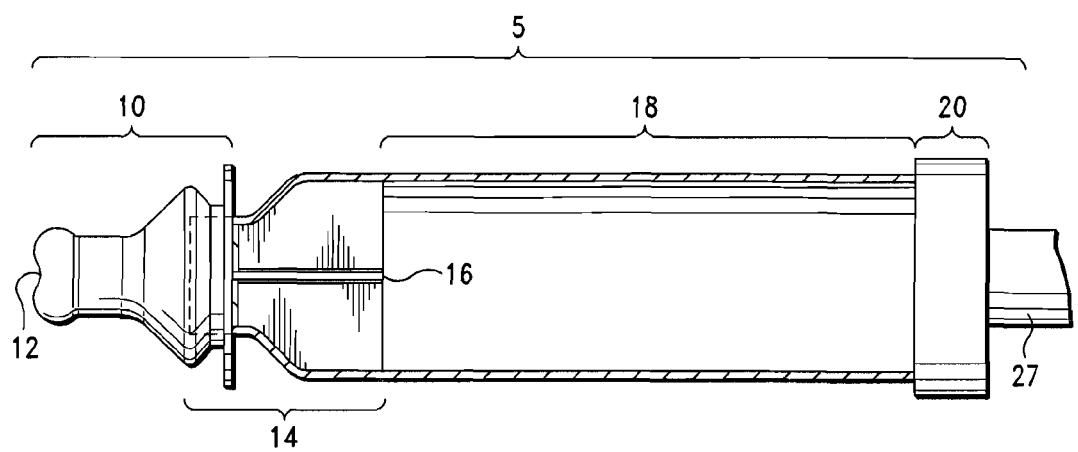
FIG. 2 is a side elevational view of the device with portions broken away and shown in cross section.
Figure 3:
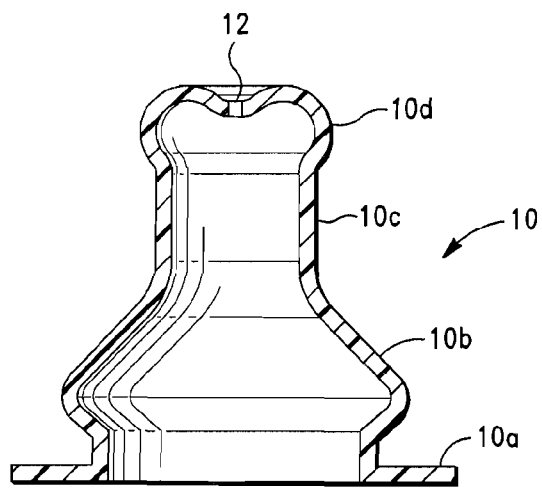
FIG. 3 is a cross sectional view of the mouthpiece of the present invention.

The intrapulmonary delivery device 5 shown in FIG. 2 comprises a mouthpiece 10, a flow rate controller 14, and a container 18. Details of the mouthpiece 10 are illustrated in FIGS. 1 and 3. The mouthpiece is a unitary structure of flexible material having an annular flat flange portion 10a, a bulbous intermediate portion 10b, the diameter of which is slightly less than the diameter of flange portion 10a, a cylindrical portion 10c and a nipple portion 10d. Nipple portion 10d has an orifice 12 at the distal end away from flange portion 10a. The mouthpiece 10 is elongated and generally tubular and is made of a flexible material that can withstand sterilization via hot water, e.g. latex or silicone rubber. Preferably, the mouthpiece is made of a clear silicone rubber-type material so that deposits of medicament or other substances within the mouthpiece can be easily viewed and removed. The orifice 12 of the mouthpiece 10 has a diameter of approximately about 3.1 mm to 8 mm and a relatively circular shape. The mouthpiece 10 has a wall thickness of approximately about 0.5 mm to 5 mm.

Figure 4A:
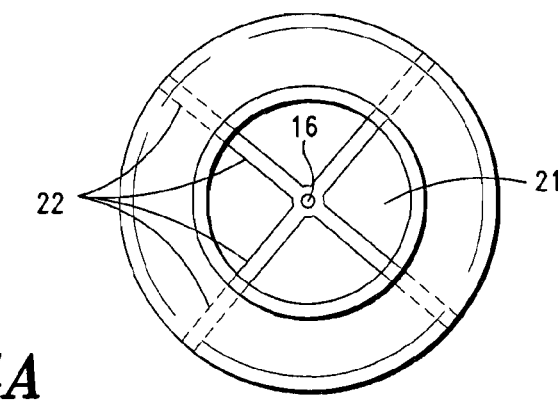
FIGS. 4A-4C are three different views of the container and flow rate controller of the present invention without the mouthpiece.
Figure 4B:
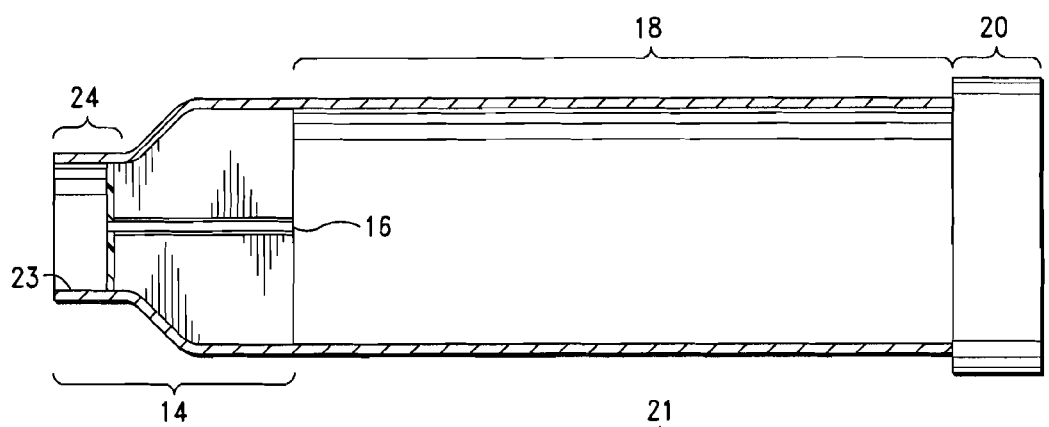
Figure 4C:
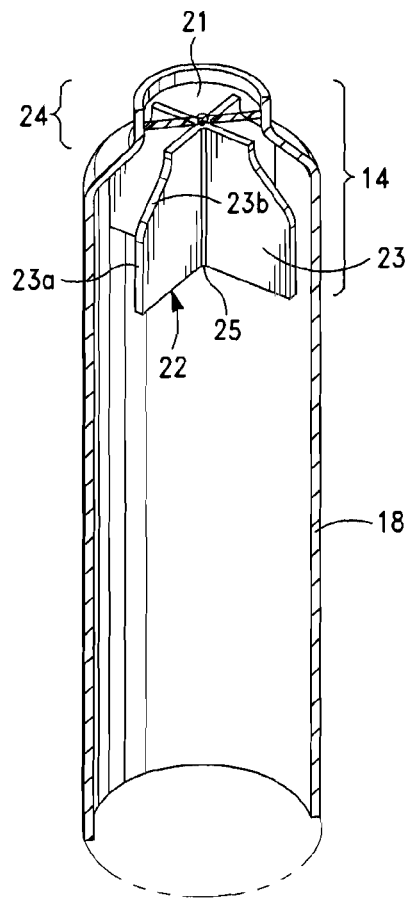
Figure 5A:
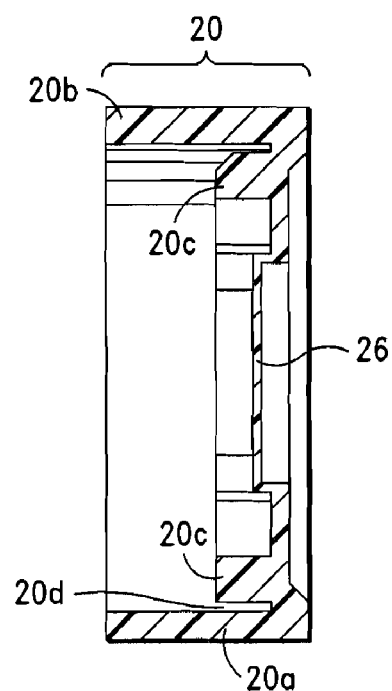
FIG. 5A is an enlarged cross sectional view of the boot structure.
Figure 5B:
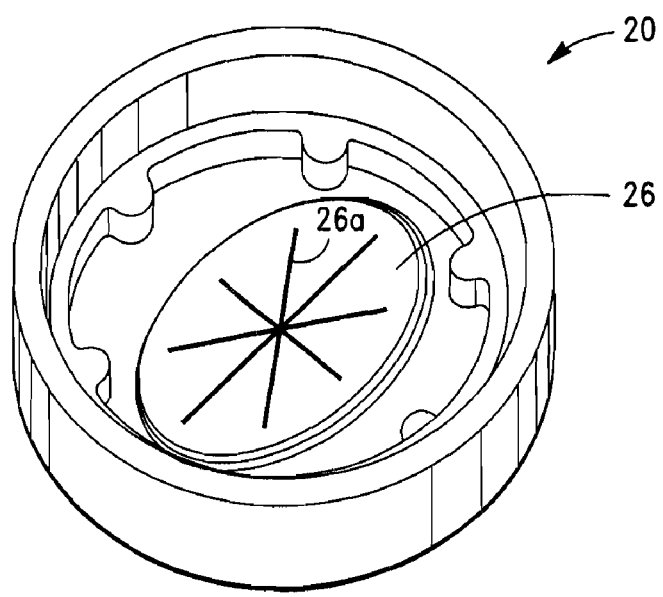
FIG. 5B is a perspective view of the interior of the boot structure showing the valve portion thereof.
Figure 6A:
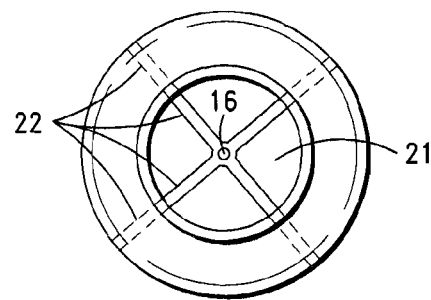
FIG. 6A is a top plan view of the container showing baffle structure.
Figure 6B:
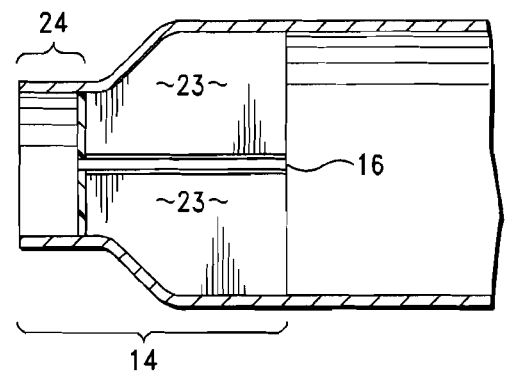
FIG. 6B is a fragmentary vertical cross section view of the container.

The container 18 is shown in FIGS. 2, 4B and 4C. Container 18 comprises a hollow cylinder of approximately about 140 mm to 160 mm in length for holding a quantity of medicament. The container 18 has a first cross sectional area and a neck portion 24 of a second cross sectional area which is less than the first cross sectional area. It is to be noted that the container wall transitions from the first to the second cross sectional area by forming an angle of approximately 45°. The container further comprises an outlet opening 23 at the end of the neck portion 24 that allows for medicament to pass through. The mouthpiece 10 is sized to fit snugly over and around the neck portion 24 of the container and is held in place by a combination of friction and elasticity. The opposite end of the container is closed by a boot 20. Boot structure 20 comprises an integral closure for the end of the container and includes side walls 20a and 20b which cooperate with a central portion 20c to present a slot 20d that frictionally engages the wall of container 18. Central portion 20c also mounts a membrane valve 26 having a plurality of slits 26a so as to accommodate the insertion of a supply tube 27 (FIG. 2). It will be appreciated that valve 26 is integral with the body of the boot 20. As best illustrated in FIGS. 2, 4A, 4B and 6C, a baffle structure 22 is coupled with neck portion 24. Baffle structure 22 comprises four vanes 23, mounted about an axial hub 25. Each of vanes 23 is spaced approximately 90° from an adjacent vane. The outboard surface of each vane has a straight section 23a which merges into an angled section 23b so that this surface generally follows the contour of container 18. An end wall 21 rigid with the vanes 23 blocks the flow of medicament from the container 18. The axial hub 25 presents a through passage 16 along its length. The diameter of passage 16 is approximately 1.5 mm to 4 mm and the length is approximately 26 mm to 32 mm. End wall 21 (FIGS. 6A and 6C) mounts baffle structure 22 rigidly with the container 18 inside the neck portion 24. It is preferred that the diameter of the mouthpiece orifice 12 is about double the diameter of passage 16.

In operation, the device of FIG. 2 is easy to use and effectively delivers medicament to the lungs of a patient. The mouthpiece 10 is connected to the neck portion 24 of the container 18 and medicament is supplied to container 18 via supply line 27. A tight fit between the mouthpiece 10 and the container 18 is essential because the transference of negative inspiratory pressure will not occur if there is a leak between the mouthpiece 10 and the container 18. The mouthpiece 10 is configured to conform to the mouth of the user as he purses his lips around the conical section 10c so that an airtight seal is formed. In this regard it will be appreciated that bulbous portion 10b forms a "stop" for the user's lips when moving in one direction, and the nipple 10d being larger in diameter than section 10c, works against accidental withdrawal of the mouthpiece when in use.

Figure 6C:
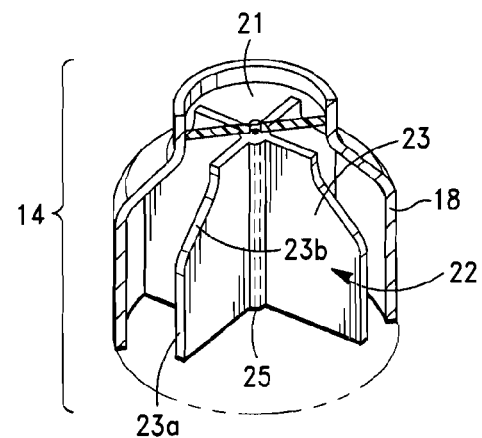
FIG. 6C is a perspective view of the flow rate controller formed by the baffle structure and the top portion of the container.

Once the user forms a seal with his or her lips around mouthpiece 10, medicament within container 18 will move into the lungs as the user inhales. Because of the specific design of baffle structure 22, greatly reduced negative pressure is required to initiate the flow of medicament through passage 16 and through orifice 12. This reduced effort results in a relatively low inspiratory flow rate which, as explained above, is desirable for maximum efficacy of the medicament. The preferred flow rate is between about 25.8 and 30.2 liters per minute (0.43 to 0.51 liters per second). While the physics of the device 5 according to the present invention are not fully understood, it is believed that the combination of the upper portion of container 18, as shown in FIG. 6C, together with baffle structure 22 form a flow rate controller 14 which promotes laminar flow and creates a type of Poiseuille gauge. The relatively high negative inspiratory pressure which is required to effect low emitted flow through passageway 16 is explained by the Poiseuille equation:

$$F = \Delta P \pi r^4 / 8 \eta l$$

where F=flow rate; r=radius of the constriction; l=length of the constriction; $\Delta P$=pressure difference driving the flow; and $\eta$=is the viscosity of air.

One alternative to the mouthpiece orifice 12 and axial hub passage 16 of the preferred embodiment described above is to make both the orifice and passage the same diameter. The passage 16 in baffle structure 22 is about 28 mm to 30 mm in length with a diameter of about 1.5 to 4 mm. The mouthpiece orifice 12 has a diameter of about 3.1 and 8 mm. Even with an orifice 12 that is the same diameter as passage 16, the effect on flow rate is only about 10% (i.e., the change in flow rate is negligible). However, doubling the size of the orifice 12 relative to the diameter of the passage 16 will produce a theoretical 16 fold increase in flow rate.

While not intending to be bound by any particular theory, it may be that human physiology is better adapted to hard sucking action on an object with the geometry of a nipple as described herein, as compared to the cylindrical or elliptical configuration of a spacer or holding chamber device of the prior art. It may also be that use of a flexible material for the mouthpiece 10 according to the present invention is better suited with respect to human physiology than a non-flexible mouthpiece in terms of generating maximum negative inspiratory pressure with minimal force. Additionally, while the mouthpiece orifice 12 of the present invention is shown in a relatively circular configuration, it will be appreciated by one skilled in the art that other configurations such as oval and elliptical can be utilized as well.

Figure 6D:
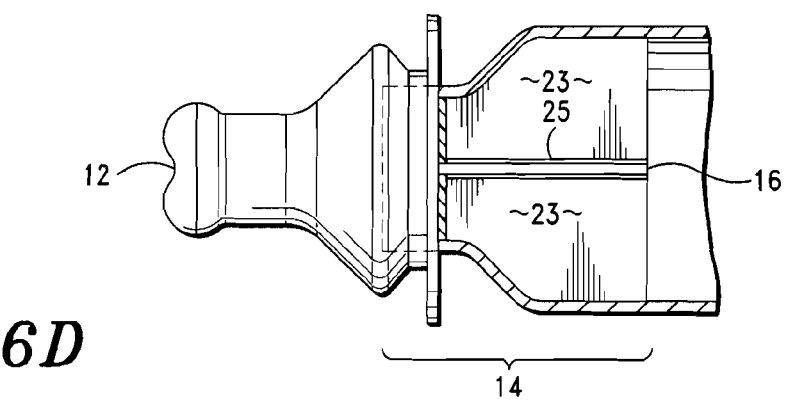
FIG. 6D is a side view of the mouthpiece placed over and around the neck portion of the container which is shown in cross section.

The mouthpiece 10 in combination with the flow rate controller 14 will work with any inhalation delivery device such as pMDIs, nebulizers, medicine cups. The mouthpiece 10 in combination with the flow rate controller 14 of the invention may also be used with other inhalation delivery devices, such as the presently available Exubera insulin delivery device. FIG. 6D illustrates a side view of the mouthpiece 10 coupled with flow rate controller 14 which may be used in conjunction with an inhalation delivery device.

Most children can inhale most of the medication in 3-4 seconds with the present invention, whereas with the prior art devices it takes a minimum of 6-8 seconds. Further, without the benefit of the invention, most children will inhale and exhale twice within the first 6-8 seconds. Usually, with prior art devices, over time (20-30 seconds or more) medication falls out of the aerosolized state, primarily due to gravity, into the portion of the spacer or holding chamber that is substantially parallel to the ground when the spacer or holding chamber is in use. This results in less medication being aerosolized, thus giving less chance for medication to be inhaled. With the present invention a greater amount of medication is inhaled in the first few seconds, before the medication falls out of its aerosolized state.

Normal tidal volume breathing (less than 30 L/min) has been shown to allow better drug deposition into the lungs. The present invention encourages young children and adults to inhale naturally at normal tidal volume rates. This is especially important with patients with Chronic Obstructive Pulmonary Disease ("COPD"), who may have difficulty generating negative inspiratory pressure. In fact, it is well known by those skilled in the art of pulmonary medicine that these groups of patients unconsciously purse their lips to enhance their breathing. The mouthpiece of the present invention naturally accommodates these patients' tendencies, permitting better generation of negative inspiratory pressure.

It will also be appreciated that the present invention encompasses a method for administering medicament via inhalation. The method is carried out utilizing a container as afore-described having a first cross sectional area and a neck portion which presents a second cross sectional area that is smaller than the first cross sectional area. The method comprises the steps of providing a flexible mouthpiece having an orifice for passage of medicament, providing a baffle structure coupled with the mouthpiece and having an axial through passage with the structure extending at least partially into the neck portion of the container. Next, the user places the mouthpiece into his or her mouth and then moves the medicament through the axial passage by inhalation. By following the afore-described method steps, the mouthpiece and baffle structure cooperate to dispense a desired quantity of medicament to the user. Preferably, the method includes providing a mouthpiece having a nipple with the orifice of the nipple having a diameter of approximately 3.1 to 8 mm. It is also preferred that the mouthpiece have a thickness of approximately 0.5 to 5 mm and that the baffle structure comprises at least three (3) vanes. The method further comprises providing a baffle structure with a through passage of approximately 1.5 to 4 mm in diameter and a length of approximately 26 to 32 mm. Preferably, the method utilizes a container having a length of 140 to 160 mm with the container comprising a boot structure which closes the end of the container opposite the outlet opening.

One of the concerns with the use of DPIs is the need to generate enough negative inspiratory pressure to de-aggregate the powdered medication found in these devices. Most patients need high negative inspiratory forces, greater than 30 L/minute to de-aggregate the medication, resulting in undesirable turbulent flow. Turbulent flow, as contrasted with laminar flow, is undesirable because it results in more oral deposition (deposition of the medicament in the mouth) rather than intrapulmonary deposition (deposition of the medicament in the lungs). The use of the present invention solves this problem if a DPI device releases the medicament into a spacer or holding chamber, e.g., the Exubera device presently on the market.

Another advantage of the present invention is time efficiency. Utilizing the prior art devices, it takes approximately 20-30 minutes to prepare and administer a single nebulization treatment. This does not take into account the time it takes to coax a relatively compliant child into submitting to the nebulization treatment. If the child is crying or combative, even more time is needed for the treatment. A crying child will have poor inspiration and will not receive the proper amount of medicament due to the poor inspiration. Using the device of the present invention, it takes approximately 8-20 seconds to complete a full inhalation treatment. While the preferred flow rate is about 25.8 to 30.2 L/minute, it is to be understood for certain applications the flow rate may range from 15 to 60 L/minute.

The method and device of the present invention are useful for delivering a wide variety of medicaments, drugs, biologically active substances, and the like, to a patient's lungs. The present invention is particularly useful for delivering high value medicaments and drugs, such as proteins and polypeptides, where efficient delivery and proper dosage are of great concern.

From the foregoing it will be seen that this invention is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A device for administering medicament for inhalation by a user, said device comprising:
   a container for holding a quantity of medicament, said container having a first cross sectional area and comprising a neck portion of a second cross sectional area which is less than said first cross sectional area, and further comprising an outlet opening at the terminus of said neck portion;
   a baffle structure comprising a plurality of rigid vanes connected to an axial hub, said hub presenting a through passage along its length, said structure further including a rigid end wall connected to said vanes and blocking the flow of medicament out of said container so that all flow must travel through the through passage to reach the user, said structure attached to said container and extending at least partially into said neck portion; and a flexible mouthpiece coupled with said container and adapted to be enclosed by the mouth of the user, said mouthpiece having an orifice for passage of said medicament.

2. The delivery device of claim 1, wherein said mouthpiece comprises a nipple.

3. The delivery device of claim 2, wherein said mouthpiece has a thickness of approximately 0.5 mm to 5 mm.

4. The delivery device of claim 1, wherein said orifice has a diameter of approximately 3.1 mm to 8 mm.

5. The delivery device of claim 1, wherein said axial hub passage has a diameter of approximately 1.5 mm to 4 mm.

6. The delivery device of claim 1, wherein said axial hub passage has a length of approximately 26 mm to 32 mm.

7. The delivery device of claim 1, wherein said baffle structure comprises at least three vanes.

8. The delivery device of claim 1, wherein said container has a length of approximately 140 mm to 160 mm.

9. The delivery device of claim 1, wherein said container has an end opposite said outlet opening with an inlet opening for receiving medicament from a source and further including a boot structure for closing said inlet opening.

10. The delivery device of claim 9, wherein said boot structure comprises a valve.

11. The delivery device of claim 1, wherein said baffle structure forms a Poiseuille gauge which delivers a flow rate within a range of about 0.25 to 1.0 L/s.

12. A device adapted to be coupled with a source of medicament for facilitating inhalation of said medicament by a user, comprising:

a flexible mouthpiece comprising a nipple shaped to conform to the mouth of said user, said nipple having an orifice for passage of said medicament; and a flow rate controller coupled with said mouthpiece comprising a rigid baffle structure comprising a plurality of rigid vanes connected to an axial hub, said hub presenting a through passage along its length, said structure further including a rigid end wall connected to said vanes and blocking the flow of medicament out of said source so that all flow must travel through the through passage to reach the user;

whereby said mouthpiece and said controller cooperate to dispense a quantity of said medicament to said user.

13. The mouthpiece of claim 12, wherein said orifice has a diameter of approximately 3.1 mm to 8 mm.

14. The mouthpiece of claim 12, wherein said nipple has a thickness of approximately 0.5 mm to 5 mm.

15. The mouthpiece of claim 12, wherein said baffle structure comprises at least three vanes.

16. The mouthpiece of claim 12, wherein said axial hub passage has a diameter of approximately 1.5 mm to 4 mm.

17. The mouthpiece of claim 12, wherein said axial hub passage has a length of approximately 26 mm to 32 mm.

18. The mouthpiece of claim 12, wherein said controller includes a housing rigid with said baffle structure.

19. The mouthpiece of claim 12, wherein said housing includes a first portion having a cross section and a second portion having a smaller cross section, said vanes extending at least partially into said second portion.

* * * * *